United States Patent [19]

Sharma et al.

[11] Patent Number: 5,378,473
[45] Date of Patent: * Jan. 3, 1995

[54] TRANSDERMAL ADMINISTRATION OF SHORT OR INTERMEDIATE HALF-LIFE BENZODIAZEPINES

[75] Inventors: Kuldeepak Sharma, Mountain View; Darth M. Dunbar, San Mateo, both of Calif.

[73] Assignee: Cygnus Therapeutic Systems, Redwood City, Calif.

[*] Notice: The portion of the term of this patent subsequent to Jul. 6, 2010 has been disclaimed.

[21] Appl. No.: 83,676

[22] Filed: Jun. 28, 1993

Related U.S. Application Data

[63] Continuation-in-part of Ser. No. 750,571, Aug. 27, 1991, Pat. No. 5,225,198.

[51] Int. Cl.⁶ .............................................. A61F 13/00
[52] U.S. Cl. .................................. 424/449; 424/447; 424/448
[58] Field of Search ..................... 424/449, 448, 447

[56] References Cited

U.S. PATENT DOCUMENTS

| | | | |
|---|---|---|---|
| 3,987,052 | 11/1976 | Hester, Jr. | 206/308 R |
| 4,557,934 | 12/1985 | Cooper | 424/128 |
| 4,973,468 | 11/1990 | Chiang et al. | 424/449 |
| 5,225,198 | 7/1993 | Sharma et al. | 424/443 |

FOREIGN PATENT DOCUMENTS

| | | |
|---|---|---|
| 61-254519 | 7/1985 | Japan . |
| 61-33129 | 2/1986 | Japan . |

OTHER PUBLICATIONS

American Hospital Formulary Service, Gerald K. Mc Evy, Ed., pp. 1197-1202, 1989.

USP Drug Information for the Health Care Professional, 10th Edition, (1990) pp. 595-602.

Abernethy et al., "Pharmacokenetics of alprazolam" *J. Clin. Psychiatry* (1983) 44(8, Sect. 2):3 pages total.

Smith et al., "Pharmacokenetics and pharmacodynamics of alprazolam after oral and IV administration" *Psychopharmacology* (1984) 84:452-456.

Shell et al., "Treatment of silent myocardial ischemia with transdermal nitroglycerin added to beta-blockers and alprazolam" *Cardiology* (1986) 4(4):697-704.

Stahl et al, "Targeting the central nervous system: new drug delivery technologies for psychotropic agents" *Psychopharmacology Bulletin* (1985) 21(3):657-662.

Cho et al., "Kenetics and equilibrium of the reversible alprazolam ring–opening reaction" *J. Pharmaceutical Sciences* (1983) 72(4):356-362.

Ormerod et al., "Effects of alprazolam on platelet activating factor-induced wealing" *British J. Dermatology* (1989) 121:411-415.

Adams et al., "Normal-phase liquid chromatographic determination of alprazolam in human serum" *Anal. Chem.* (1984) 56(9):1590-1594.

Yalkowsky et al., "In-vitro method for detecting precipitation of parenteral formulations after injection" *J. Pharmaceutical Sciences* (1983) 72(9):1014-1017.

*Primary Examiner*—D. Gabrielle Phelan
*Attorney, Agent, or Firm*—Morrison & Forrester

[57] ABSTRACT

Method and laminated composite for administering short or intermediate half-life benzodiazepines such as alprazolam or triazolam transdermally to treat conditions such as anxiety in the case of alprazolam and insomnia in the case of triazolam. The composite comprises an impermeable backing layer and a reservoir layer containing the benzodiazepine and a permeation enhancer combined with a solvent-based acrylic polymer adhesive with the amounts of benzodiazepine and enhancer being sufficient to cause the benzodiazepine to pass through the skin at a rate in excess of about one $\mu g/cm^2/hr$.

6 Claims, 2 Drawing Sheets

TRANSDERMAL ADMINISTRATION OF SHORT OR INTERMEDIATE HALF-LIFE BENZODIAZEPINES

CROSS-REFERENCE TO RELATED APPLICATION

This application is a continuation-in-part of copending U.S. Application Ser. No. 07/750,571, filed Aug. 27, 1991, now U.S. Pat. No. 5,225,198.

DESCRIPTION

1. Technical Field

This invention relates to methods and devices for administering short- and intermediate-acting benzodiazepines, particularly alprazolam and triazolam, transdermally.

2. Background

Alprazolam (8-chloro-1-methyl-6-phenyl-4H-1,2,4-triazolo(4,3-a)(1,4)benzodiazepine) is a short to intermediate half-life benzodiazepine drug. It is sold commercially in the U.S. under the brand name Xanax in the form of tablets for treatment of anxiety, depression, and panic disorders. U.S. Pat. No. 3,987,052 describes the preparation and oral administration of alprazolam. It is given orally in doses of 0.25 to 0.5 mg with a maximum dose up to 4 mg for adults. Therapeutic plasma concentrations are typically in the 17 to 30 ng/ml range. (*USP Drug Information for the Health Care Professional*, page 595, 10th Ed., 1990.) The pharmacokinetics and pharmacodynamics of alprazolam after oral and intravenous administration are reported in *J. Clin. Psychiatry* (1983) 44 (8, Sec. 2) and *Psychopharmacology* (1984) 84:452–456.

Triazolam (8-chloro-6-(2-chlorophenyl)-1-methyl-4H-1,2,4-triazolo-(4,3-a) -1,4-benzodiazepine is a short half-life benzodiazepine drug. It is sold commercially in the U.S. under the brand name Halcion in the form of oral tablets for treatment of insomnia. It is given orally at doses of 125–250 μg.

Japanese Pat. Pub. 61254519 describes formulations of drugs with polyvinyl acetate and sulfoxides such as dimethylsulfoxide for transdermal administration. The publication suggests administering benzodiazepines from such formulations but does not mention alprazolam or triazolam. Similarly, Japanese Pat. Pub. 61033129 describes pharmaceutical formulations of various drugs in sesquiterpene alcohol and a polar compound for transdermal administration. It, too, mentions benzodiazepines but says nothing about alprazolam or triazolam.

The present invention is directed to achieving noninvasive sustained administration of short and intermediate half-life benzodiazepines, particularly alprazolam or triazolam, at therapeutically effective levels by delivering them in combination with a skin permeation enhancer transdermally.

DISCLOSURE OF THE INVENTION

Accordingly, one aspect of the invention is a method for providing short or intermediate half-life benzodiazepine therapy to an individual in need of such therapy comprising administering a therapeutically effective amount of said benzodiazepine to the individual transdermally through a predetermined area of skin over a sustained time period at a controlled rate in combination with a sufficient amount of a permeation enhancer to enable the benzodiazepine to permeate the area of skin at a rate in excess of about one $\mu g/cm^2/hr$.

Another aspect of the invention is a laminated composite for administering a short or intermediate half-life benzodiazepine to an individual transdermally through a predetermined area of skin of the individual comprising:

a) a backing layer that is substantially impermeable to the benzodiazepine; and b) a reservoir layer comprising a solvent-based acrylate polymer, the benzodiazepine dissolved in said polymer, and a permeation enhancer that increases the permeability of the skin to the benzodiazepine dissolved in said polymer, the basal surface of said reservoir layer being adapted to be adhered to said area of skin and wherein the amounts of the benzodiazepine and enhancer in said reservoir layer are sufficient to enable a therapeutically effective amount of the benzodiazepine to be administered at a rate in excess of about 1 $\mu g/cm^2/hr$ to the individual through said predetermined area of skin over a sustained time period.

Another aspect of the invention is an edge-sealed laminated composite for administering a short or intermediate half-life benzodiazepine to an individual transdermally through a predetermined area of intact skin comprising (a) a backing layer that is substantially impermeable to the benzodiazepine and forms the top surface of the device;

(b) a substrate layer underlying the backing layer that is sealed at its edge to the backing layer to form a pouch therebetween;

(c) a liquid formulation of the benzodiazepine and a permeation enhancer that increases the permeability of the skin to the benzodiazepine contained within the pouch; and (d) means for adhering the device to the skin in benzodiazepine delivery relationship thereto, wherein the amounts of benzodiazepine and enhancer in the liquid formulation are sufficient to enable a therapeutically effective amount of benzodiazepine to be administered at a rate in excess of about 1 $\mu g/cm^2/hr$ to the individual through said predetermined area of intact skin over a sustained time period.

MODES FOR CARRYING OUT THE INVENTION

Figure 1:
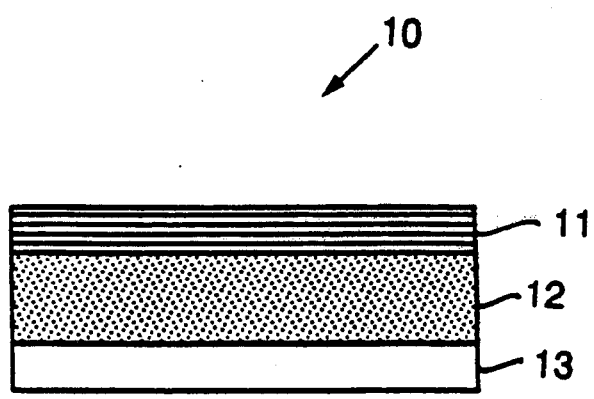
FIG. 1 shows one embodiment of a skin patch for administering a short or intermediate half-life benzodiazepine transdermally.

As used herein, the term "transdermal" intends both percutaneous and transmucosal administration, i.e.., passage of a short or intermediate half-life benzodiazepine through intact unbroken skin or mucosal tissue into circulation.

As used herein, the term "short and intermediate half-life benzodiazepines" is intended to include those benzodiazepines that have an elimination half-life of less than about 24 hrs, preferably less than about 16 hrs. Short and intermediate half-life benzodiazepines include alprazolam, bromazepam, lorazepam, oxazepam, temazepam, and triazolam.

As used herein, the term "benzodiazepine therapy" means those medical conditions for which the particular short- or intermediate-acting benzodiazepine is indicated. For instance, in the case of alprazolam, such therapy includes, without limitation, the treatment of anxiety, depression, panic, or substance (e.g., alcohol, nicotine) withdrawal symptoms. Correspondingly, in the case of triazolam, such therapy includes, without limitation, insomnia.

As used herein, the term "therapeutically effective amount" intends that dose of the benzodiazepine that provides the desired therapy. In the case of alprazolam, the dose is normally in the range of about 0.75 to 6 mg per day and may vary depending upon the patient and the indication being treated. In the case of triazolam, the dose is normally in the range of 0.1 to 1.0 mg/day, more usually 0.25 to 0.50 mg/day.

As used herein, the phrase "sustained time period" means at least about one day and will typically intend a period in the range of about 1 to 3 days in the case of alprazolam and at least about 16 hr, typically 2 to 24 hr, in the case of triazolam.

As used herein, the term "predetermined area or skin" intends a defined area of intact unbroken living skin or mucosal tissue. That area will usually be in the range of about 20 cm$^2$ to about 100 cm$^2$, more usually 20 cm$^2$ to 60 cm$^2$.

As used herein, the phrase "benzodiazepine delivery relationship" intends that the device contacts the skin in a manner that establishes a diffusive pathway from the benzodiazepine reservoir to the skin.

As used herein, the term "controlled rate" intends a time course of benzodiazepine administration to circulation that is predetermined and governed by the area of skin through which the drug is passed, the permeability of the skin to the drug, and the activity of the drug maintained in the formulation over the duration of administration.

"Permeation enhancement" as used herein relates to an increase in the permeability of skin to the benzodiazepine as compared to the permeability of skin to the benzodiazepine as measured by the diffusion cell apparatus described in the examples using the benzodiazepine formulated in propylene glycol as a control.

Based on the published pharmacokinetic data on alprazolam, applicants estimated that skin flux in the range of at least about 1 μg/cm$^2$/hr would be required to deliver therapeutically effective amounts of alprazolam transdermally through a practical skin area (i.e., less than about 100 cm$^2$). However, when applicants measured the in vitro flux of alprazolam through skin from a propylene glycol solution, they found the flux was several-fold less than the flux required to deliver a therapeutic amount of the drug through such an area of skin. Applicants thus attempted to enhance the flux of the drug through skin by using various permeation enhancers and found that the skin flux could be increased to levels that make transdermal administration practical with some of those enhancers. This finding enabled applicant to develop formulations and laminated composites that permit short and intermediate half-life benzodiazepines to be administered transdermally through a practical area of skin at rates that result in plasma levels of the benzodiazepine that provide desired therapeutic effects.

One type of laminated composite for administering alprazolam or triazolam transdermally to humans is shown in FIG. 1. This composite, generally designated 10, comprises a backing lamina 11, a reservoir lamina 12, and a release liner lamina 13.

The backing layer provides a protective covering for the composite and may itself be a single layer or a multiplicity of layers. For instance, if the composite is to be worn for periods in excess of a day or two, it is desirable to make the backing from an elastomeric polymer such as polyurethane, polyether amide, or copolyester. For devices that are intended to be worn for shorter durations, the backing may be made from relatively flexible but not elastomeric occlusive polymers such as polyester, polyethylene, and polypropylene. The thickness of the backing layer will normally be in the range of about 15 microns to about 250 microns.

The reservoir lamina is preferably composed of the benzodiazepine, a permeation enhancer selected from the group consisting of an ester of the formula $[CH_3(CH_2)_mCOO]_nR$ in which m is an integer from 8 to 16, preferably 8 to 12, most preferably 10; n is 1 or 2, preferably 1; and R is a lower alkyl ($C_1$-$C_3$) residue which may be substituted with 0 to 2 hydroxyl groups, a fatty alcohol of 8 to 16 carbon atoms, fatty acids of 8 to 16 acids, mixed vegetable oil (a mixture of coconut oil and soybean oil in a weight ratio between 9:1 and 1:9), or mixtures thereof, and a solvent-based acrylate polymer adhesive. The drug is present in the layer in excess of its solubility in the two other components. It will normally constitute about 1% to about 10% by weight of the lamina. The enhancer is present in the layer in amounts ranging between about 2 to about 20% by weight. The preferred esters of the above formula are lower alkyl ($C_1$-$C_3$) esters of lauric acid, with propylene glycol monolaurate (PGML) and glyceryl monooleate being particularly preferred. Lauryl or olelyl alcohol are preferred fatty alcohols and lauric or oleic acid are preferred fatty acids. It will be appreciated by those skilled in the art that commercially available PGML is normally a mixture of propylene glycol monolaurate, propylene glycol dilaurate and either propylene glycol or methyl laurate or both. Thus "propylene glycol monolaurate" is intended to encompass the pure compound as well as the mixture that is sold commercially. The thickness of the reservoir layer will normally be in the range of 20 microns to 150 microns, preferably 25 microns to 100 microns.

The reservoir lamina plays two functional roles, namely, it is a reservoir for the benzodiazepine and the enhancer, and its adhesive and basal surface provides the means by which the composite is affixed to the skin. The basal release liner lamina 13 is a protective coating for the reservoir lamina during storage and prior to affixation to the skin. This layer is removed from the composite before the composite is affixed to the skin.

The reservoir layer may be formulated by conventional methods known in the field of transdermal drug delivery devices and the three layers assembled into a laminated composite by like methods.

Figure 2:
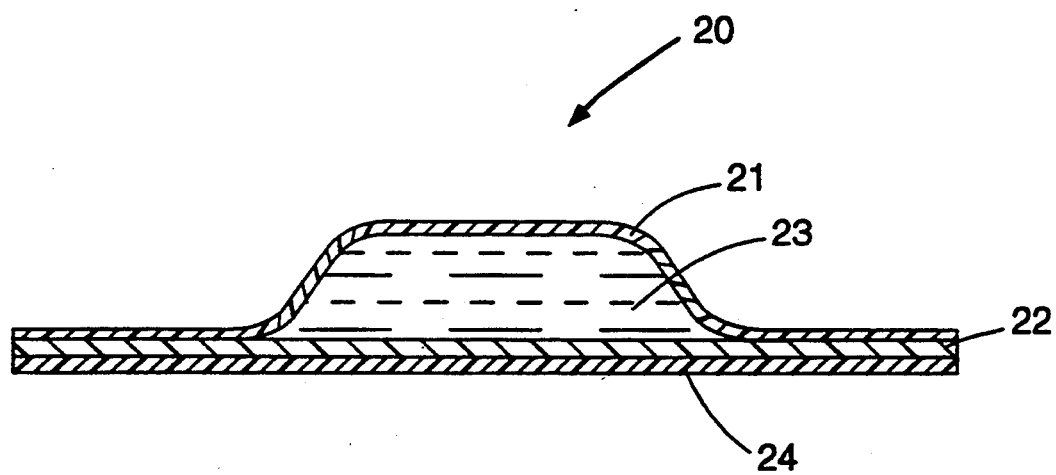
FIG. 2 shows another embodiment of a skin patch for administering a short or intermediate half-live benzodiazepine transdermally.

FIG. 2 depicts an alternative device structure for administering the benzodiazepine transdermally. The device is a liquid reservoir-type and is generally designated 20. It comprises a top impermeable backing layer 21, an underlying benzodiazepine and permeation enhancer permeable substrate layer 22 that is sealed (heat or otherwise) at its edge to the overlying backing layer to form a pouch that contains a liquid formulation of the benzodiazepine and permeation enhancer, and a pressure-sensitive adhesive layer 24 that serves as the means for affixing the device to the skin. Alternative means such as a peripheral ring of adhesive, an adhesive overlay, or straps may be used to affix the device to the skin. Substrate layer 22 may be formed of conventional microporous or dense polymers that are permeable to drugs. When placed on the skin, the benzodiazepine and enhancer diffuse from the liquid formulation in pouch 23 through the substrate layer and adhesive layer to the skin.

Specific embodiments of the invention are further illustrated by the following examples. These examples are not intended to limit the invention in any manner.

Example 1

In Vitro Skin Flux of Alprazolam From Various Liquid Formulations

Alprazolam Formulations

Formulations of alprazolam (obtained from Fermion Corp.) in propylene glycol (PG) were used. Candidate permeation enhancers (10% w/w) were added to the control formulation of the drug in propylene glycol alone. Excess alprazolam was present.

Skin Permeation Methodology

Human cadaver skin was used for in vitro permeation studies. Frozen skins were thawed and epidermal layers (stratum corneum and viable epidermis) were separated from the full-thickness skin by immersion in water at 60° C. for 2 minutes. This epidermis was either used immediately for diffusion studies or stored at −20° C. for later studies.

The skin sections were mounted carefully between the half cells of a modified Franz cell. The receiver compartment was filled with 10% ethanol, 90% saline solution. The experiment was initiated by placing 500 μl test alprazolam formulation in the donor compartment. The Franz cells were placed in an incubator at 32° C. At predetermined times, a 1 ml aliquot was withdrawn from the receiver and replaced with fresh receptor solution. Samples were assayed by HPLC using UV detection at 229 nm. Adequate chromatographic resolution was achieved using a Zorbax Rx C-18 column. The mobile phase was 65% methanol:acetonitrite (1:3) with 35% water containing 0.01% phosphoric acid.

Skin flux (μg/cm$^2$/hr) was determined from the steady-state slope of a plot of the cumulative amount of alprazolam permeated through the skin versus time.

Results

The permeation of alprazolam from the test formulations through cadaver skin at 32° C. is presented in Tables 1 and 2 below. (Two sets of tests were made using different skins.)

TABLE 1

| No. | Formulation | Skin Flux (μg/cm$^2$/hr) |
|---|---|---|
| 1. | PG alone (control) | 0.19 (0.22, 0.16) |
| 2. | PG alone (a) | 0.15 (0.13, 0.16) |
| 3. | 10% PGML | 15.80 ± 5.93 |
| 4. | 10% Ethanol | 1.55 (1.33, 1.78) |
| 5. | 10% Transcutol | 0.54 ± 0.10 |
| 6. | 10% Glyceryl Monooleate | 2.80 ± 0.90 |
| 7. | 10% Disodium Sulfosuccinate | 0.62 ± 0.23 |
| 8. | 10% Cocaamido Propyl Betaine | 0.57 ± 0.34 |

(a) Receptor Media = Normal saline alone

TABLE 2

| No. | Formulation | Skin Flux (μg/cm$^2$/hr) |
|---|---|---|
| 1. | PG (control) | 0.34 ± 0.07 |
| 2. | 10% Isopropyl Myristate | 2.92 ± 1.52 |
| 3. | 10% Lauryl Alcohol | 29.92 ± 6.75 |
| 4. | 10% Softigen 767 | 0.67 (0.94, 0.40) |
| 5. | 10% Tetraethylene glycol dimethyl ether | 0.23 ± 0.07 |
| 6. | 10% Mixed Vegetable Oil* | 5.09 ± 0.02 |
| 7. | 10% Lauric Acid, N,N,-dimethylamide | 4.43 (2.16, 6.69) |
| 8. | 10% Neopentyl glycol dicaprate | 1.88 ± 0.21 |

*Coconut-soybean mix, Drewmulse D-4661, Stepan, Maywood, New Jersey

As indicated, significant enhancement of skin flux was achieved only with fatty acid ester, fatty alcohol, fatty acid and mixed vegetable oil enhancers.

Example 2

In Vitro Skin Flux of Alprazolam From Laminated Composites

Prototype laminated composites were prepared as follows. Five percent of alprazolam, 15% permeation enhancer, and a solvent-based acrylate polymer (Gelva 788) were mixed thoroughly, using a vortex to obtain homogeneous suspension of the alprazolam in the polymer/enhancer solution. A 75 micron thick film of this mix was cast into a polyester release liner (3M #1022) with a knife. The cast film was dried at 70° C. for 2 hr, die cut to 3 cm$^2$, the release liner was removed and the film was placed on the skin section of the diffusion cell. Alprazolam skin flux was measured as in Example 1. The results of these tests are given in Table 3 below.

TABLE 3

| No. | Reservoir Composition | Av. Skin Flux (μg/cm$^2$/hr) |
|---|---|---|
| 1. | 5% alprazolam — Gelva 788 | 0.69 ± 0.01 |
| 2. | 5% alprazolam + 15% PGML — Gelva 788 | 1.36 ± 0.06 |
| 3. | 5% alprazolam + 15% glyceryl monooleate — Gelva 788 | 1.51 ± 0.05 |
| 4. | 5% alprazolam + 15% mixed vegetable oil — Gelva 788 | 1.42 ± 0.07 |
| 5. | 5% alprazolam + 15% glyceryl monooleate — 5% PGML — Gelva 788 | 1.76 ± 0.36 |
| 6. | 5% alprazolam — 15% mixed vegetable oil + 5% PGML — Gelva 788 | 1.69 ± 0.07 |

Example b 3

In Vitro Skin Flux of Triazolam From Various Liquid Formulations

Triazolam formulations were prepared and tested as in Example 1. The details of these formulations anti the results of the tests are shown in Table 4 below.

TABLE 4

| No. | Formulation | Skin Flux (μg/cm$^2$/hr) |
|---|---|---|
| 1. | Triazolam saturated in PG | 0.091 ± 0.031 |
| 2. | Triazolam (saturated) + 10% Lauryl Alcohol in PG | 13.23 ± 8.31 |
| 3. | Triazolam (saturated) + 10% PGML in PG | 8.642 ± 7.52 |
| 4. | Triazolam (saturated) + 10% Glyceryl Monooleate in PG | 1.166 ± 0.63 |
| 5. | Triazolam (saturated) + 10% Mixed Vegetable Oil in PG | 6.71 ± 5.25 |

These data confirm that fatty acid esters, fatty alcohols, and mixed vegetable oils effectively enhance the skin flux of short and intermediate half-life benzodiazepines.

Example 4

In Vitro Skin Flux of Alprazolam

From Liquid Reservoir Devices

Rectangular prototype devices were made by edge-sealing an aluminized polyester backing layer to a microporous high density polyethylene membrane on three sides. A layer of adhesive was then placed over the microporous membrane. Liquid alprazolam formulations were placed between the layers via the open side, and the fourth side was then sealed. These devices were placed on the skin section of a diffusion cell and alprazolam skin flux was measured as in Example 1. Details of the formulations and the results of the tests are given in Table 5 below.

TABLE 5

| Drug Formulation | Adhesive | Avg. Skin Flux ($\mu g/cm^2/hr$) |
|---|---|---|
| 3% alprazolam + 10% PGML in PG | 4201 | 3.88 |
| 3% alprazolam + 10% oleic acid in PG | Morstik 607 | 5.94 |
| 3% alprazolam + 10% oleyl alcohol in PG | Morstik 607 | 6.22 |
| 3% alprazolam + 10% PGML in PG | Morstik 607 | 3.65 |

Example 5

In Vitro Skin Flux of Alprazolam

From Laminated Composites

Other laminated composites were prepared as follows. Alprazolam (Xa) and PG or a mixture of PG and PGML were mixed thoroughly. Glycerol monooleate (GMO) was then added to the mixture and the combined mixture was mixed further. A solvent based acrylate adhesive (Morstik 607) was added to the mixture and the resulting combined mixture was mixed thoroughly to obtain a clear solution. A 75 micron thick film of this solution was cast onto a polyester backing with a knife. The cast film was dried at 70° C. for 2 hr to remove the solvent present in the adhesive. A release liner layer was applied to the exposed surface of the film and 20 cm² pieces were die cut from the resulting laminated composite.

After removal of the release liner layer, skin flux studies of each composite was carried out as in Example 2. The details of the composition of the matrix layer of these composites and the results of the flux tests are given in Table 6 below.

TABLE 6

| Matrix Formulation | Avg. Skin Flux ($\mu g/cm^2/hr$) |
|---|---|
| 3% Xa + 5% PGML + 15% PG + 15% GMO | 3.30 ± 0.64 |
| 3% Xa + 10% PGML + 5% PG + 5% GMO | 3.02 ± 0.64 |
| 3% Xa + 20% PG + 20% GMO | 4.76 ± 1.28 |
| 3% Xa + 20% PG + 5% GMO | 1.74 ± 0.16 |
| 3% Xa + 5% PG + 20% GMO | 3.77 ± 0.19 |
| 3% Xa + 10% PGML + 20% PG + 5% GMO | 4.25 ± 0.30 |
| 3% Xa + 10% PGML + 20% PG + 20% GMO | 7.09 ± 0.83 |
| 3% Xa + 10% PGML + 5% PG + 20% GMO | 4.14 ± 1.42 |
| 3% Xa + 5% PG + 5% GMO | 1.43 ± 0.19 |
| 3% Xa + 5% PGML + 15% PG + 15% GMO | 5.16 ± 1.27 |
| 3% Xa — 5% PGML — 20% PG — 15% GMO | 5.78 ± 0.89 |
| 3% Xa — 5% PGML — 20% PG — 15% GMO | 3.85 ± 0.14 |
| 5% Xa — 5% PGML — 15% PG — 15% GMO | 7.36 ± 0.95 |

TABLE 6-continued

| Matrix Formulation | Avg. Skin Flux ($\mu g/cm^2/hr$) |
|---|---|
| 10% Xa — 5% PGML — 15% PG — 15% GMO | 5.90 ± 1.37 |

Modifications of the above-described modes for carrying out the invention that are obvious to those skill in the field of transdermal drug delivery devices are intended to be within the scope of the following claims.

We claim:

1. A method for providing short or intermediate half-life benzodiazepine therapy to a human patient in need of such therapy comprising applying a transdermal drug delivery device for administering a therapeutically effective amount of the benzodiazepine to the patient through a predetermined area of intact skin over a sustained time period at a controlled rate in combination with a sufficient amount of a permeation enhancer to enable the benzodiazepine to permeate the area of skin at a rate in excess of about one $\mu g/cm^2/hr$, wherein the benzodiazepine has an elimination half-life of less than about 24 hours and wherein the permeation enhancer is selected from the group. consisting of an ester of the formula $[CH_3(CH_2)_mCOO]_nR$ in which m is an integer from 8 to 16, n is 1 or 2 and R is a lower alkyl ($C_1$-$C_3$) residue; a fatty alcohol; a fatty acid; a mixed vegetable oil; or mixtures thereof.

2. The method of claim 1 wherein the benzodiazepine is alprazolam and the alprazolam is administered at a rate of about 0.75 to 6 mg/day.

3. The method of claim 1 wherein the benzodiazepine is triazolam and the triazolam is administered at a rate of 0.1 to 1.0 mg/day.

4. The method of claim 1 wherein the area of skin is 20 to 60 cm², the benzodiazepine is alprazolam and the alprazolam is administered at a rate of at least about 100 $\mu g/hr$.

5. A laminated composite for administering a short or intermediate half-life benzodiazepine to an individual transdermally through a predetermined area of skin of the individual comprising:
   (a) a backing layer that is substantially impermeable to the benzodiazepine and forms the top surface of the device;
   (b) a substrate layer underlying the backing layer that is sealed at its edge to the backing layer to form a pouch therebetween;
   (c) a liquid formulation of the benzodiazepine and a permeation enhancer that increases the permeability of the skin to the benzodiazepine contained within the pouch; and
   (d) means for adhering the device to the skin in benzodiazepine delivery relationship thereto, wherein the amounts of benzodiazepine and enhancer in the liquid formulation are sufficient to enable a therapeutically effective amount of the benzodiazepine to be administered at a rate in excess of about 1 $\mu g/cm^2/hr$ to the individual through said predetermined area of intact skin over a sustained time period;
   wherein the benzodiazepine has an elimination half-life of less than about 4 hours and wherein the permeation enhancer is selected from the group consisting of an ester of the formula $[CH_3(CH_2)_mCOO]_nR$ in which m is an integer from 8 to 16, n is 1 or 2 and R is a lower alkyl ($C_1$-$C_3$) residue; a fatty alcohol; a fatty acid; a mixed vegetable oil; or mixtures thereof.

6. The laminated composite of claim 5 wherein the benzodiazepine is alprazolam and the permeation enhancer is propylene glycol monolaurate, glycerol monooleate, oleic acid, oleyl alcohol, or mixtures thereof.

* * * * *